(12) United States Patent
Sjoquist et al.

(10) Patent No.: US 9,855,126 B2
(45) Date of Patent: Jan. 2, 2018

(54) IMPLANT TISSUE FIXATION SYSTEM AND METHOD

(71) Applicant: Boston Scientific Scimed, Inc., Maple Grove, MN (US)

(72) Inventors: Scott L. Sjoquist, Minnetonka, MN (US); Benjamin Y Arcand, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 289 days.

(21) Appl. No.: 14/148,459

(22) Filed: Jan. 6, 2014

(65) Prior Publication Data

US 2014/0194679 A1 Jul. 10, 2014

Related U.S. Application Data

(60) Provisional application No. 61/748,826, filed on Jan. 4, 2013.

(51) Int. Cl.
*A61F 2/00* (2006.01)

(52) U.S. Cl.
CPC .......... *A61F 2/0063* (2013.01); *A61F 2/0045* (2013.01)

(58) Field of Classification Search
CPC .... A61F 2/0063; A61F 2/0045; A61F 2/0004; A61F 2/0031; A61F 2002/0063; A61B 2017/00805; A61B 2017/00349; A61B 2017/12018
USPC ................ 606/139–141, 151; 600/30, 36
See application file for complete search history.

(56) References Cited

U.S. PATENT DOCUMENTS

| | | | |
|---|---|---|---|
| 2009/0105728 A1* | 4/2009 | Noda | A61B 17/12013 606/139 |
| 2010/0261955 A1* | 10/2010 | O'Hern | A61B 17/0401 600/37 |
| 2010/0274074 A1* | 10/2010 | Khamis | A61B 17/00234 600/37 |
| 2011/0112357 A1* | 5/2011 | Chapman | A61B 17/0401 600/37 |
| 2012/0253362 A1* | 10/2012 | Noda | A61B 17/12013 606/140 |

* cited by examiner

*Primary Examiner* — Christine H Matthews
*Assistant Examiner* — Kaylee Wilson
(74) *Attorney, Agent, or Firm* — Brake Hughes Bellermann LLP

(57) ABSTRACT

Various embodiments of a mesh or implant system are provided. In certain embodiments, a tissue fixation device is included. The tissue fixation device can include an eyelet structure having an opening and one or more teeth adapted to grasp tissue to secure the implant in place.

8 Claims, 2 Drawing Sheets

IMPLANT TISSUE FIXATION SYSTEM AND METHOD

PRIORITY AND RELATED APPLICATION

This Application claims priority to and the benefit of U.S. Provisional Patent Application No. 61/748,826, filed Jan. 4, 2013, which is hereby incorporated fully herein by reference.

FIELD OF THE INVENTION

The present invention relates generally to surgical methods and apparatus and, more specifically, to implantable mesh, sling or implant devices for use in treating incontinence or other pelvic disorders.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

In certain circumstances, suturing and suture knot tying can add significant time to procedures and can also be challenging for less skilled surgeons. Additionally, suturing laparoscopically can sometimes be very difficult and time consuming.

There is a desire to obtain a minimally invasive yet highly effective implantable implant that can be used to treat incontinence, and/or pelvic organ prolapse and other conditions.

SUMMARY OF THE INVENTION

The present invention describes pelvic mesh implants and methods for treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness.

In certain embodiments, the mesh implants include one or more eyelet structures that are molded onto or otherwise provided with the mesh. These eyelets can be designed with features and dimensions to pass small portions of tissues in the body. The passage of the tissue can be unidirectional so that the tissue passing through the eyelet engages a portion of the eyelet and is prevented from passing back through the eyelet and becoming disengaged. The eyelet can be designed with an open center to provide space for tissue to be passed through. The eyelet can also have direction teeth configured to let a bite or small piece of tissue pass unidirectionally through the eyelet and become locked in place.

Methods for passing the tissue through the eyelet include using the vacuum of a surgical suction device to draw the tissue through the eyelet, or simply using a pair of surgical pick-ups or tweezers to grasp the tissue through the eyelet such that the tissue can be pushed or pulled through.

In other embodiments, a specialized tool can be included that inverts the eyelet teeth temporarily through the eyelet opening. When the inverted teeth are pressed against the tissue and then allowed to revert to the original configuration, they can draw the tissue through the eyelet opening and lock the tissue in place.

In another embodiment, the mesh and eyelet configuration can include a more planar design in which the eyelet teeth can be created by slicing a film of polymer (e.g., sheet) in addition to a more traditional molding method. When the tissue is pulled through the jagged slit, the teeth are deformed in the direction of the pull. The tissue then occupies the space in the eyelet opening or slit gap and the teeth prevent the tissue from passing back out the eyelet. Such a construct can allow for a lower profile, and a more flexible design.

The eyelet structure for passing and grasping tissue provides a potential sutureless and quick attachment configuration for a mesh or like pelvic implant device. Time spent manipulating and tying suture knots can be avoided.

DETAILED DESCRIPTION OF PREFERRED EMBODIMENTS

Figure 1:
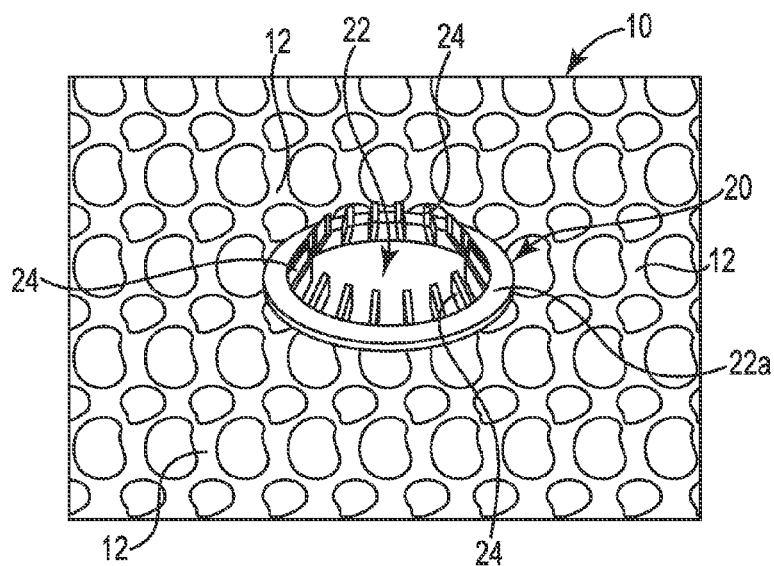
FIGS. 1-1b show an eyelet tissue grasping device provided with an implant, in accordance with embodiments of the present invention.
Figure 1A:
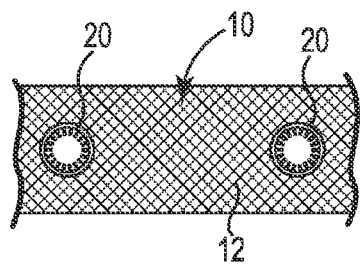
Figure 2:
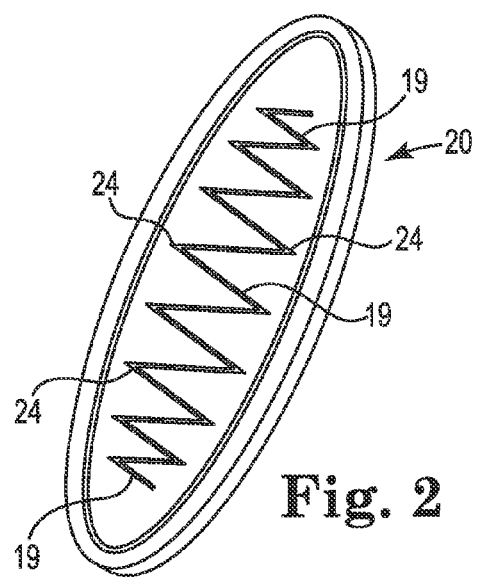
FIGS. 2-2b show a generally planar eyelet tissue grasping device provided with an implant, in accordance with embodiments of the present invention.
Figure 2A:
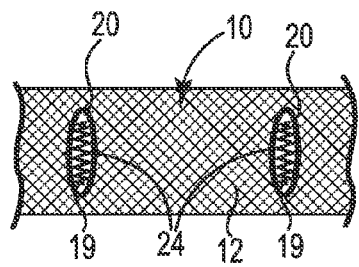
Figure 2B:
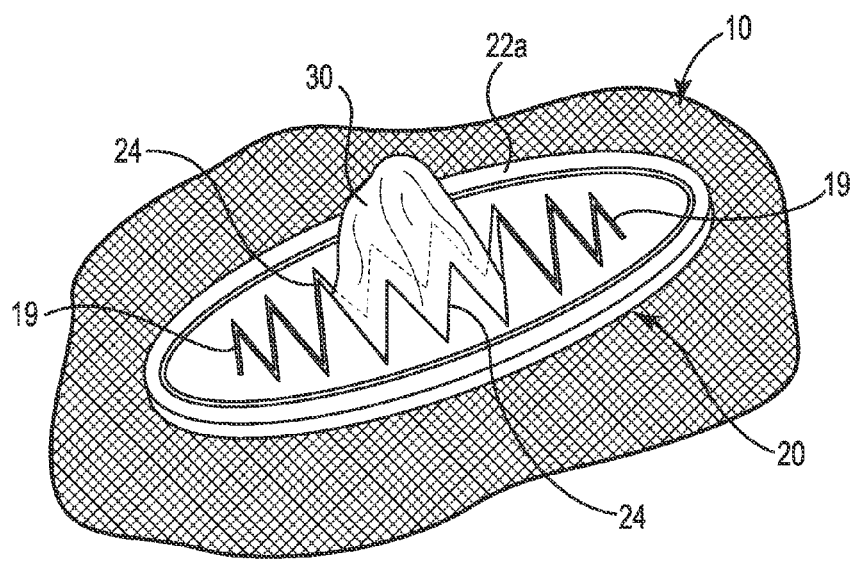

Referring generally to FIGS. 1-2b, various embodiments of implantable sling or mesh support systems 10 and implant methods are shown. In general, the implant systems 10 can include support portions 12, anchoring portions, and extensions. Various portions of the implant systems 10 can be constructed of polymer materials, including mesh constructs including a plurality of filaments or members to define a lattice form. Certain embodiments can be constructed of or from a film or sheet material of polypropylene, polyethylene, fluoropolymers or like compatible materials, e.g., into a molded generally planar structure or from a thin generally planar film or sheet material. Examples of acceptable polymer materials available in constructing or forming the implant systems and its components can include polypropylene, polyethylene, fluoropolymers or like biocompatible materials.

The various implants 10 or systems, features and methods detailed herein are envisioned for use with many known implant and repair systems (e.g., for male and female), features and methods, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261 and WO 2007/097994, and U.S. Patent Publication Nos. 2011/0144417, 2010/0105979, 2002/151762 and 2002/147382. Accordingly, the above-identified disclosures are fully incorporated herein by reference in their entirety.

In certain embodiments, the mesh implant 10 can include one or more eyelet structures 20. The eyelets 20 can be molded onto the mesh, or separately provided. These locking eyelets 20 can be designed with features and dimensions to pass and grasp small amounts of tissue 30 in the body. The passage of the tissue can be unidirectional so that the tissue passing through the eyelet 20 engages a portion of the eyelet and is prevented from passing back through the eyelet and becoming disengaged. The eyelet 20 can include an open center 22 to provide space for tissue to be passed through. The eyelet 20 can also have directional teeth or members 24 configured to let the tissue pass unidirectionally through the eyelet 20 and become locked in place.

Figure 1B:
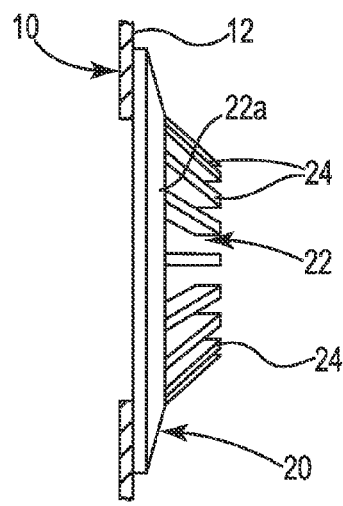

As shown in FIGS. 1 and 1b, the teeth can be configured to angle inward toward the open center 22 and out above a top surface 22a of the eyelet 20. As such, a construct is provided for grasping or catching the tissue upon entry into the open center 22. The eyelet 20 can take on a myriad of sizes and shapes, including circular, rectangular, oval, undulating, elongate, and the like. The ends of the teeth members 24 can include barbs, angled surfaces, hooks or like features to further facilitate tissue grasping.

Methods for passing the tissue through the eyelet 20 include using a vacuum of a surgical suction device to draw the tissue through the eyelet 20, or simply using a pair of surgical pick-ups or tweezers to grasp the tissue through the eyelet 20 such that the tissue can be pulled through. In addition, the eyelet 20 portion of the implant can be pressed down on the tissue such that the manual force causes the tissue to push through the open center 22 for grasping or tissue engagement.

In other embodiments, a specialized tool can be included that inverts the eyelet teeth 24 temporarily through the eyelet opening 22. When the inverted teeth 24 are pressed against the tissue and then allowed to revert to the original configuration, they can draw the tissue through the eyelet opening 22 and lock the tissue in place.

In another embodiment, as shown in FIGS. 2-2b, the implant 12 and eyelet 20 configuration can include a more planar design in which the eyelet teeth 24 can be created by slicing a film of polymer (e.g., sheet) provided within the eyelet 20, in addition to a more traditional molding method. When the tissue 30 is pulled through the jagged slit 19 (rather than angled teeth extending out from the plane of the eyelet 20 or its surface 22a) the teeth 24 expand away from the slit 19 gap. The teeth 24 are deformed in the direction of the tissue pull or push. The tissue 30 then occupies the space in the eyelet opening 22 and the teeth 24 of the slit 19 prevent the tissue 30 from passing back out the eyelet 20. Such a construct can allow for a lower profile, and a more flexible design and implementation.

The slit 19 can take on a variety of shapes and sizes such that some or all of the angle changes along the slit provide relatively pointed, sharped or barbed structures capable of grasping tissue during deployment at the target treatment site.

The implant systems 10, their various components, structures, features, tools, materials and methods may have a number of suitable configurations as shown and described in the previously-incorporated references. Various methods and tools for introducing, deploying, anchoring and manipulating implants to treat incontinence and prolapse as disclosed in the previously-incorporated references are envisioned for use with the present invention as well. Further, the system and its components or structures can be constructed of known and compatible materials know to those skilled in the art, including metals, polymers, and the like.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

What we claim is:

1. A method of treating a pelvic condition in a patient, comprising:
   providing a mesh implant including an eyelet, the eyelet including a polymer sheet disposed within the eyelet, the polymer sheet having a slit, the slit defining a plurality of tissue engagement members when tissue is pulled through the slit, the plurality of tissue engagement members being generally planar in a first position;
   introducing the mesh implant into a pelvic region of the patient;
   positioning the mesh implant to support pelvic tissue of the patient; and
   forcing pelvic tissue through the slit in a first engagement direction such that the pelvic tissue forces the plurality of tissue engagement members in a second position angled away from the generally planar first position such that the pelvic tissue does not substantially move out of the slit in a second direction generally opposite to the first engagement direction.

2. The method of claim 1, wherein the slit includes a zigzagging slit.

3. The method of claim 1, wherein the mesh implant includes a plurality of filaments.

4. A method of treating a pelvic condition in a patient, comprising:
   providing a mesh implant including an eyelet, the eyelet including a polymer sheet disposed within the eyelet, the polymer sheet having a slit, the slit defining a plurality of jaggedly angled tissue engagement members when tissue is pulled through the slit;
   introducing the mesh implant into a pelvic region of the patient;
   positioning the mesh implant to support pelvic tissue of the patient; and
   directing pelvic tissue through the slit in a first engagement direction such that the jaggedly angled tissue engagement members angle outward and the pelvic tissue becomes captured therebetween.

5. The method of claim 4, wherein the eyelet is a first eyelet, the mesh implant including a second eyelet, the second eyelet having a polymer sheet disposed within the second eyelet, the polymer sheet of the second eyelet having a slit.

6. The method of claim 4, wherein the plurality of tissue engagement members extend inward.

7. The method of claim 4, wherein the mesh implant is generally elongate.

8. The method of claim 4, wherein the eyelet is molded to the mesh implant.

* * * * *